US011065371B2

(12) United States Patent
Steen

(10) Patent No.: US 11,065,371 B2
(45) Date of Patent: Jul. 20, 2021

(54) FLOW RESTRICTOR FOR SURGICAL DEVICE

(71) Applicant: Johnson & Johnson Surgical Vision, Inc., Santa Ana, CA (US)

(72) Inventor: Mark E. Steen, Santa Ana, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 252 days.

(21) Appl. No.: 16/216,960

(22) Filed: Dec. 11, 2018

(65) Prior Publication Data

US 2019/0184071 A1 Jun. 20, 2019

Related U.S. Application Data

(60) Provisional application No. 62/598,974, filed on Dec. 14, 2017.

(51) Int. Cl.
*A61M 39/24* (2006.01)
*A61M 1/00* (2006.01)
*A61F 9/007* (2006.01)

(52) U.S. Cl.
CPC ....... *A61M 1/0035* (2014.02); *A61F 9/00736* (2013.01); *A61F 9/00745* (2013.01);
(Continued)

(58) Field of Classification Search
CPC .......... A61B 2217/005; A61F 9/00736; A61M 1/0035; A61M 2039/2433; A61M 2205/3341; A61M 2210/0612
See application file for complete search history.

(56) References Cited

U.S. PATENT DOCUMENTS 5,012,841 A 5/1991 Kueffer et al.
5,348,036 A 9/1994 Oksanen et al.
(Continued)

FOREIGN PATENT DOCUMENTS

WO 0219896 A2 3/2002
WO 2004000130 A2 12/2003
(Continued)

OTHER PUBLICATIONS

International Search Report and Written Opinion for Application No. PCT/US2018/065060, dated May 24, 2019, 12 pages.

*Primary Examiner* — Deanna K Hall
(74) *Attorney, Agent, or Firm* — Johnson & Johnson Surgical Vision, Inc.

(57) ABSTRACT

An apparatus, system and method for providing a flow restrictor suitable for inclusion in an aspiration flow of an ocular surgical device. The flow restrictor includes a conical valve head suitable for insertion into a valve stage, wherein, upon the insertion, the valve head at least substantially impedes the aspiration flow; a flexible spider membrane having a plurality of valve passages that open and close with the flexation of the membrane, wherein the membrane is connective with the valve head and forces the insertion of the valve head into the valve stage proportionally to the aspiration flow; a circular receiving plate for receiving the aspiration flow, wherein the circular receiving plate imparts the proportional insertion to the membrane; and a plurality of ribs integral to at least one of the valve head and the valve stage that provides a minimum for the aspiration flow when the insertion is full.

20 Claims, 4 Drawing Sheets

(52) U.S. Cl.
CPC ....... *A61M 39/24* (2013.01); *A61B 2217/005* (2013.01); *A61M 2039/2433* (2013.01); *A61M 2205/3341* (2013.01); *A61M 2210/0612* (2013.01)

(56) References Cited

U.S. PATENT DOCUMENTS

| | | |
|---|---|---|
| 6,478,781 B1 | 11/2002 | Urich et al. |
| 6,905,108 B2 | 6/2005 | Hall et al. |
| 7,758,546 B2 | 7/2010 | Injev et al. |
| 8,801,653 B2 | 8/2014 | Maaskamp et al. |
| 9,561,321 B2 | 2/2017 | Sorensen et al. |
| 10,286,202 B2 * | 5/2019 | Mosier ................. A61M 39/24 |
| 10,610,678 B2 * | 4/2020 | Martin ................. F16K 15/147 |
| 2005/0113741 A1 | 5/2005 | Huang et al. |
| 2006/0224163 A1 | 10/2006 | Sutton |
| 2010/0292631 A1 | 11/2010 | Holden et al. |
| 2015/0164690 A1 | 6/2015 | Peterson et al. |

FOREIGN PATENT DOCUMENTS

| | | |
|---|---|---|
| WO | 2009076717 A1 | 6/2009 |
| WO | 2014195927 A1 | 12/2014 |

* cited by examiner

SECTION A-A

SECTION B-B

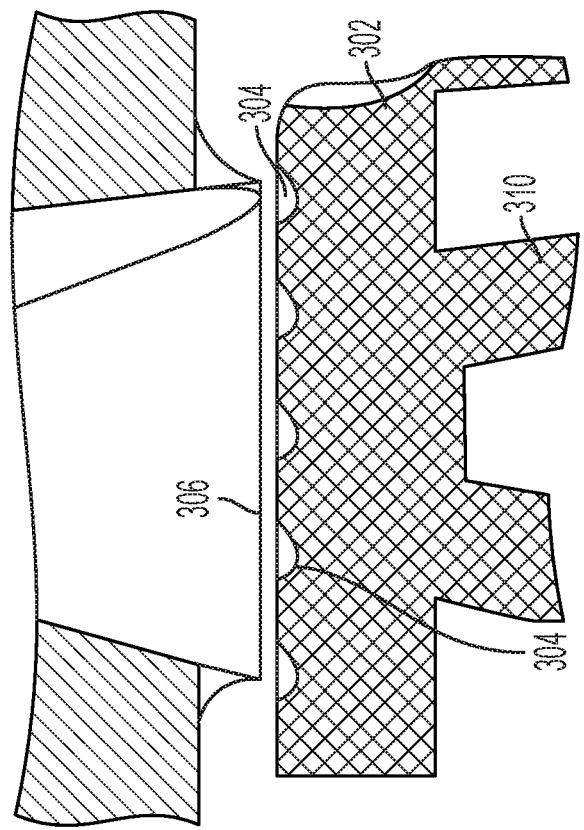
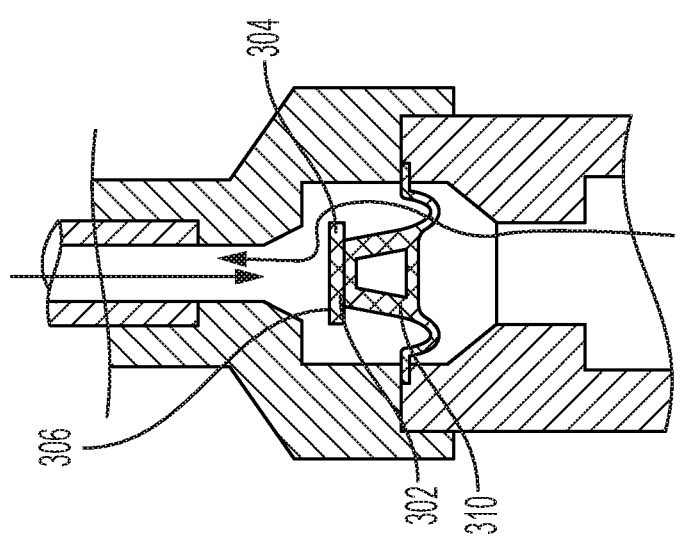
FIGURE 3B
FIGURE 3A

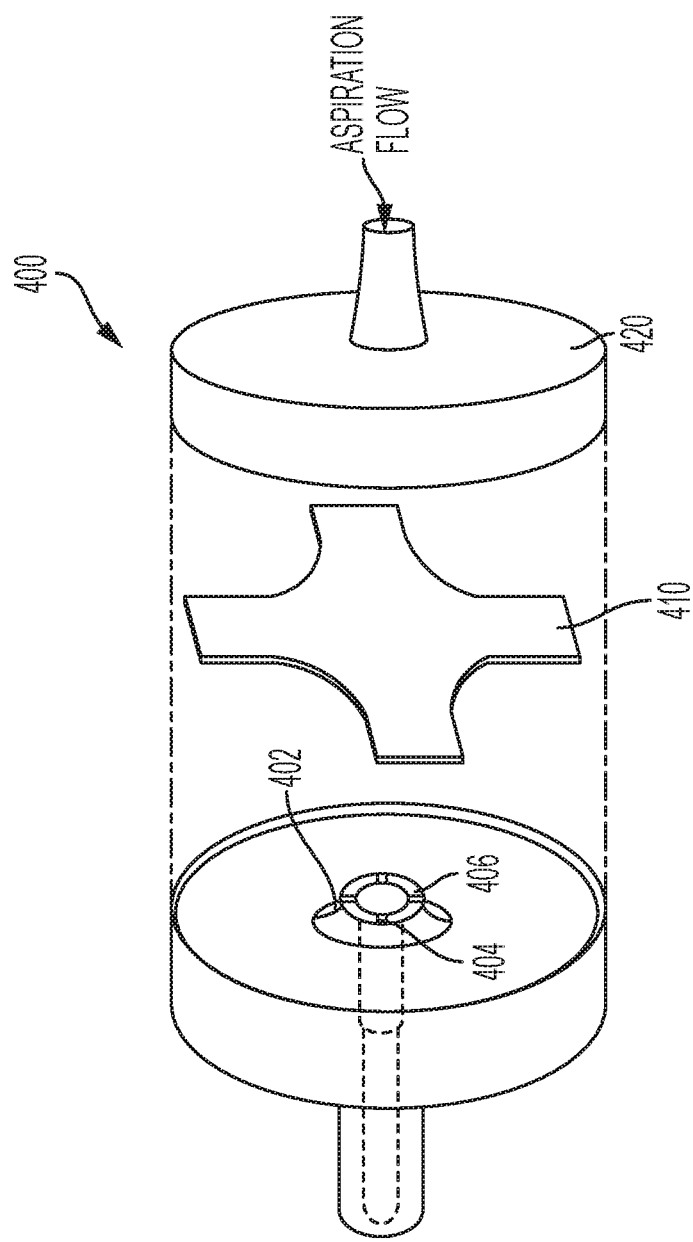

FLOW RESTRICTOR FOR SURGICAL DEVICE

CROSS REFERENCES TO RELATED APPLICATIONS

This application claims the benefit under 35 U.S.C. § 119(e) of U.S. Provisional Application No. 62/598,974, filed on Dec. 14, 2017, which is incorporated herein by reference in its entirety.

FIELD OF THE INVENTION

The instant disclosure relates to surgical vacuum and, more particularly, to a post occlusion flow restrictor for ocular surgical devices.

BACKGROUND

Surgery on the human eye has become commonplace in recent years. Many patients pursue eye surgery as an elective procedure, such as to avoid the use of contacts or glasses, and other patients may find it necessary to pursue surgery to correct an adverse condition in the eye. Such adverse conditions may include, for example, cataracts or presbyopia, as well as other conditions known to those skilled in the art that may negatively affect elements of the eye. For example, a cataract may increase the opacity of the lens of the eye, causing impaired vision or blindness.

The anatomy and physiology of the human eye is well understood. Generally speaking, the structure of the human eye includes an outer layer formed of two parts, namely the cornea and the sclera. The middle layer of the eye includes the iris, the choroid, and the ciliary body. The inner layer of the eye includes the retina. The eye also includes, physically associated with the middle layer, a crystalline lens that is contained within an elastic capsule, referred to herein as the lens capsule, or capsular bag.

Image formation in the eye occurs by entry of image-forming light to the eye through the cornea, and refraction by the cornea and the crystalline lens to focus the image-forming light on the retina. The retina provides the light sensitive tissue of the eye.

Functionally, the cornea has a greater, and generally constant, optical power in comparison to the crystalline lens. The power of the crystalline lens, while smaller than that of the cornea, may be changed when the eye needs to focus at different distances. This change, or "accommodation," is achieved by changing the shape of the crystalline lens. Accommodation thus includes the making of a change in the focus of the eye for different distances. For example, in order to change the shape of the crystalline lens for accommodation, the ciliary muscles may relax to cause ligaments that support the crystalline lens to relax, thereby allowing the crystalline lens to become more rounded. Of course, the need for surgery may also arise should the crystalline lens become incapable of such accommodation.

Correction of defects or degradation in the aspects of the eye, such as those mentioned above, may be performed surgically, as referenced. For example, phacoemulsification of a non-functional or deficient crystalline lens is a medically recognized technique which generally includes making of a corneal incision and the insertion of a hand held surgical implement, i.e., a handpiece, which includes a needle, or "tip", that is ultrasonically driven to emulsify the eye's crystalline lens. The handpiece is typically equipped to not only emulsify the lens, but further to provide a vacuum for aspiration of the emulsified lens, and also to provide irrigation for the insertion of fluids into the eye's chamber in order to maintain an acceptable pressure within the eye, thus preventing collapse of or other damage to the eye.

More particularly, this irrigation may be provided in order to maintain normal pressure within the eye during surgery as the aspiration vacuums the emulsified material from the eye. For example, a balanced salt solution (BSS) may be provided as an irrigation fluid (such as typically from an elevated chamber) as the tip emulsifies the lens and the aspirator removes the emulsified lens.

Importantly, this irrigation, and the aspiration of fluid and material from the eye, must be carefully monitored and maintained, such as by a surgeon or a phacoemulsification system, in order to maintain normal pressure within the eye during surgical procedures. For example, an underpressure condition may cause distortion of the eye, which may interfere with surgical procedures. On the other hand, overpressure may cause severe damage to the eye.

One such overpressure condition, post-occlusion surge (POS), is a well-known phenomenon. During normal surgical conditions (i.e., when the phacoemulsification tip is not occluded), the vacuum level of the aspirator is relatively low. However, in a POS condition, occlusion at the emulsifying tip of the handpiece allows the aspirating vacuum to build (such as to a preset vacuum shutoff limit) until the blockage is broken. Upon breaking of the occlusion, stored energy in the tubing causes a rapid surge flow from the patient's eye, which can cause adverse effects to the structures within the eye. While mini-surges may happen hundreds of times during a typical phacoemulsification surgery, a major POS event may only happen occasionally, but with very significant adverse effects to the patient.

By way of non-limiting example, the posterior capsule of the eye may be torn upon a POS. This tear may occur because of the explosive release of the elastic potential of the aspiration system as the occlusion is breached, which overwhelms the inflow of irrigation and, in its most severe form, can completely evacuate the anterior chamber of the eye.

Yet further, because irrigation continues during occlusion, the pressure continues to rise in the anterior chamber. Meanwhile, the vacuum continues to draw as referenced above, thereby causing the aforementioned negative pressure to build in the tubing. This creates a potentially dangerous pressure gradient, which causes the pressure in the eye to drop yet more precipitously after the occlusion is broken. It is nearly impossible for a surgeon to react in a timely enough manner to a POS to prevent eye damage when such conditions occur.

Electro-mechanical controls for POS occurrences are typically too slow to react to a significant surge condition. Resistance elements, such as small bore needles (small ultrasonic tips) and distributed resistance of rigid small-bore tubing that is less compressive, have been effectively used to somewhat limit the surge condition following POS. However, the use of such variations in tubing size and similar resistance elements can also increase the likelihood of blockages in the tubes.

In addition to variably-bored, i.e., small bore, tubing, numerous other flow restriction devices have entered the market. These devices include duck-bill valves, restrictive needle devices, and coiled tubing that depends on the physics properties of curved fluid flow. Duckbill valves, for example, are open to nominal reverse flow, but close under rapid reverse flow, and thus do not allow for refluxation of inadvertent aspiration of wanted tissue. Inline fixed restrictors often employ small needles that are protected by screen mesh to keep particles from blocking the needle. These devices are very effective at the onset of a surgery, but as the screen becomes blocked by aspirant, the rate of flow may reduce to unacceptable levels. Sufficient refluxation may then also be blocked by the particles in the screen, as the reverse flow particles block the needle or are ejected back into the eye. The coiled tubing solution is bulky and adds complication to the fluid response, slowing the surgical removal of tissue.

Thus, all of the foregoing known solutions to the POS issue, whether located in the aspiration module cassette or at the handpiece, restrict flow, and while such restriction may prevent some POS damage, these known solutions also restrict aspiration rate and the efficiency of tissue removal. Moreover, most of these devices must be removed after phacoemulsification. The removal maximizes the performance of the subsequent phases of an ocular procedure, which typically have little risk of POS. Needless to say, this need for removal decreases the convenience, speed and efficiency of the overall surgical process.

Thus, a need exists for a flow restrictor suitable to improve ocular surgical performance and also to address POS during ocular surgery.

BRIEF DESCRIPTION OF THE DRAWINGS

The accompanying drawings are included to provide a further understanding of the disclosure, and are incorporated into and thus constitute a part of this specification. The drawings illustrate disclosed embodiments and/or aspects and, together with the description, serve to explain the principles of the disclosure. In the drawings:

FIGS. 3A and 3B are cross-sectional views of an exemplary flow restrictor according to the embodiments; and FIG. 4 is an exploded view of an exemplary flow restrictor according to the embodiments.

DETAILED DESCRIPTION

Figure 1:
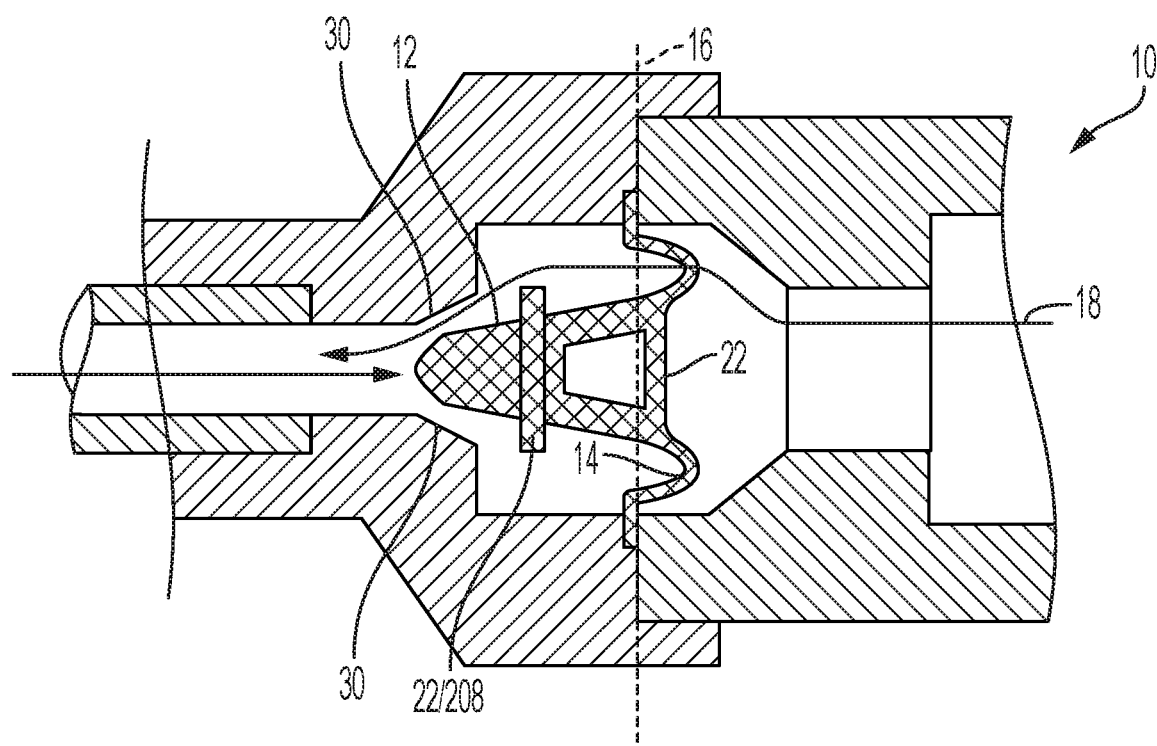
FIG. 1 is a cross-sectional view of an exemplary flow restrictor according to the embodiments.

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical surgical, and particularly ophthalmic surgical, devices, systems, and methods. Those of ordinary skill may recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "upon", "connected to" or "coupled to" another element or layer, it may be directly on, upon, connected or coupled to the other element or layer, or intervening elements or layers may be present, unless clearly indicated otherwise. In contrast, when an element or layer is referred to as being "directly on," "directly upon", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements or aspects, these elements or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, component, region, layer or section discussed below could be termed a second element, component, region, layer or section without departing from the teachings of the disclosure.

The embodiments include a flow restrictor, which may take the form of a multi-stage variable-flow restrictor, i.e., a multistage valve. Upon a large POS, the valve may immediately and substantially "close", as the flow may push at least an aspect of the valve hard against a valve seat. The closure is substantial and not complete because, in the embodiments, a small flow is maintained even in the event of full valve closure. For example, the valve or the valve seat, as discussed below, may be ribbed (a term used herein to include ribs, grooves, slots, and the like), wherein the ribs may be of such a size so as to maintain what is deemed an adequate flow even upon valve closure. That is, the ribs preferably do not allow a complete shut off of aspiration flow.

Yet further, an additional valve stage aspect may include a capability for insertion and retraction of one or more other of the valve stages, such as through the use of a spider-membrane/spring. Such a spider membrane may itself provide valving, such as by providing one or more passthroughs, and may proportionally react to the flow by "closing" an additional valve stage.

Should particles collect close to the disclosed flow restrictor, the blockage will have minimal effect on the restrictor performance, as the "main" valve is constantly retracting, in accordance with the proportional response of the spider membrane, responsive to the flow itself, thereby allowing the aspirated tissue to readily pass under normal flow conditions. Accordingly, the constant flow maintained throughout the disclosed embodiments by the multistage valve causes there to be no collection areas for particles on or about the flow restrictor.

In normal operation, such as during normal operation or minor surge conditions, the multi-stage valve proportionately and minimally or partially closes in response to the level of any surge condition. During phacoemulsification, there is a regular cadence of particles and various levels of minor surge, as referenced above, and the disclosed multi-stage valve will not substantially impede flow under such conditions, but instead will simply proportionally protect the eye in relation to this typical cadence of particles. Indeed, these minor pressure fluctuations are expected and have minimal effect on surgical outcome. The constant variable restriction of the disclosed multi-stage valve helps effectively stabilize the pressure in the eye during such minor pressure fluctuations, thus reducing any particularly detrimental pressure fluctuations without adversely affecting the surgical process.

Further, during venting or reflux, the disclosed flow restrictor also allows unrestricted back flow, i.e., reflux, in all surgical conditions. That is, in the reverse flow condition, the disclosed multistage valve opens to full reverse flow without back pressure, thus again not impeding the positive aspects of known surgical procedures.

However, in a POS condition, the disclosed multistage valve may proportional close as the surge condition increases, without need of human controller intervention. Thus, without negating the positive aspects of known surgical methodologies, the disclosed embodiments do negate the negative aspects of POS, thus improving surgical outcomes.

FIG. 1 is a side-view cross-section of a multi-stage variable flow restrictor 10 having a conical valve "main" stage 12. In the normal flow condition illustrated, a spider membrane/diaphragm spring 14 is connective with the main valve stage 12, and may be proportionally retracted along an axis 16 centered on the end points of the membrane during normal or minor surge aspiration flow 18, wherein the retraction occurs toward the aspiration generation flow point. When the membrane is fully retracted, the valve is substantially open, and the valving may be substantially provided by flowthroughs of the spider membrane stage 14.

Also included in this exemplary embodiment may be a circular plate 22, which may be provided at the base of the conical valve 12 or in conjunction with a passthrough substantially at the center of the spider membrane 14, which circular plate 22 may adjust the action of the main valve 12 in direct response to the rate of flow against the valve head. A larger area of the circular plate increases the sensitivity to smaller flow rates, and a smaller circular plate reduces the sensitivity of the valve to flow rate. Similarly and as detailed with greater particularity below, the spider membrane may provide the circular plate as a flat surface that has one or more variable/flexible passages therethrough, and it may be this flat surface that receives the pressure of advancing flow to insert the conical valve 12.

Under high flow conditions, the plate 22 thus forces the spider membrane 14 to flex towards the conical valve seat 30, and the conical valve head 12 thus proportionally "closes" against the valve seat 30 responsive to the extent of flow 18. During lower flow rates, the spider 14 keeps the valving substantially open and also assures availability of reverse flow, such as for venting and reflux. Among other things, this allows the valving to release tissue that has been inadvertently aspirated during phacoemulsification or IA by the surgeon.

As will be understood, upon a large POS event, the conical main valve 12 immediately and substantially "closes" as the surge flow pushes the main valve 12 hard against the valve seat 30. This condition is illustrated in FIG. 2A, wherein the spider 14 has moved the conical valve 12 to the insertion position, i.e., has itself flexed with the flow toward the conical valve seat 30 from its fixed end points.

In short, should a significant surge condition occur, the sudden flow thus moves the conical valve 12 into the valve seat 30 proportionally to the magnitude of the surge condition. The embodiments thus provide a temporary and variable resistance to the in-rush flow. If there is no in-rush or surge, the valving remains open, as the spider 14 provides some limited valving but retracts the main valve 12. Since the flow restriction is variable and is limited under such normal operating conditions, the outflow remains at a relative steady flow.

Figure 2A:
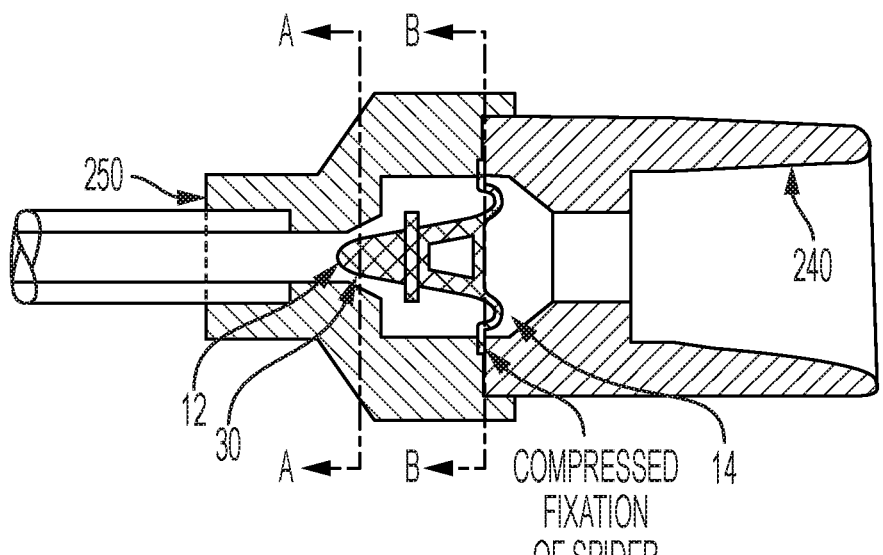
FIGS. 2A, 2B, and 2C are cross-sectional views of an exemplary flow restrictor according to the embodiments.
Figure 2B:
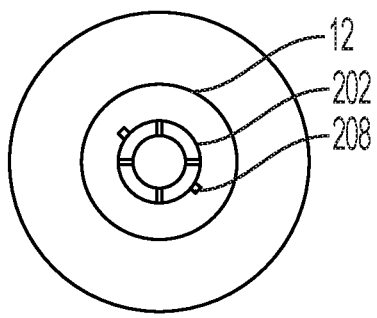

As illustrated in FIG. 2B, which is a cross-sectional illustration taken along line A-A in FIG. 2A, at least a small flow may be maintained even at a high surge condition, i.e., even in the event of the conical valve closure illustrated in FIG. 2A. This is because of ribs 202 or valleys present in either the outer surface of conical valve 12 or on the sealing surface of the main valve seat 30, which do not allow complete shut-off of flow as some of the flow will always leach through the ribs 202 or valleys even in the event that main valve 12 completely seats within valve 30 upon insertion by spider 14.

Of note in the illustrated embodiments, even should particles collect about the flow restrictor 10, they will have minimal effect on the variable restrictor's performance, as the valve 12 retracts and allows the particles to pass under normal flow, and thus there are no collection areas as the flow is always at least partially open. To enhance this retraction under normal flow, one or more bumpers 208, as illustrated in FIG. 2B, may be used to force the conical valve 12 out of the valve seat 30 and to help set the minimal flow distance.

Thus, during minor surge conditions, the main valve 12 proportionately closes in response to the surge condition. And during high POS events, the main valve 12 closes substantially in a proportional response to the higher surge. Thus, a constant variable restriction of the multi-stage valve 10 helps effectively stabilize the eye's chambers and reduce detrimental pressure fluctuations.

Figure 2C:
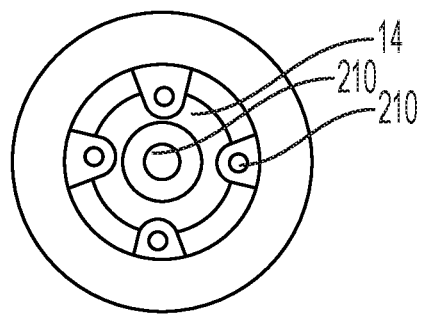

The variable restriction capability of the embodiments is illustrated with greater particularity in the cross-sectional illustration of FIG. 2C, taken along line B-B in FIG. 2A. In the illustration, multiple flow passages 210 are shown through the spider membrane 14, and these flow passages 210 may include a thin flow passage at the center of the membrane. Each of the membrane flow passages 210 may change the level of flow restriction correspondent to the linear translation of the spider membrane 14—that is, the passages may provide valves that are flexibly opened and closed as the spider membrane 14 flexibly translates.

Accordingly, the spider membrane 14 may be, by way of no-limiting example, a flexible membrane, such as a rubber membrane, having one or more passages 210 that change dimensionally as the spider flexes, thereby providing increased or decreased flow using flapped or thinned areas by which the passages 210 open and close upon flexing of spider 14 to vary flow restriction. The circumscribed ribbed (or valley) surface allows the central conical valve (restrictor) to translate linearly into a conical valve seat based on the flexing of the spider membrane.

The disclosed multi-stage flow restrictor device may, by way of non-limiting example, replace or be present in conjunction with the typical aspiration luer fitting 240 used to connect the aspiration source to the handpiece. It may also be placed within the handpiece, or within flow module cassette tubing at a control console associated with the handpiece, as may be appreciated by the skilled artisan.

By way of example with respect to a luer fitting, a luer connection 240 may be present on one end, as shown in FIG. 2A, and an external tubing slip fitting 250 may be bonded in place, such as by solvent adhesive or laser welding, on the other end of the aspirator. These two cylindrical components may be bonded together so as to compress or otherwise affix at least the end points of the spider 14 therewithin. Yet further, a luer-related surge restrictor may be permanently attached as described, or may be configured as a luer-to-luer connection, which would allow the surgeon/operator to remove and insert it at will.

FIGS. 3A and 3B illustrate an additional exemplary embodiment, in which the conical valve 302 comprises a flat plate, and the ribs 304 about the conical valve 302 now comprise a waffle surface on either the valve 302, such as a rubber valve, or on the valve seat, which may be a rigid valve seat 306. The disc valve 302 may be mounted on the spider spring/membrane 310, as discussed above, and under high flow conditions the disc valve 302 may be forced into hard contact with the valve seat 306. As is particularly evident in FIG. 3B, the waffle surface may allow a minimum level of flow even during full contact with the valve seat, thus creating a variable restriction to flow that prevents surge. In this configuration, the spider may also be a circumferential spring around the plate valve, thus allowing the valve to be more compact.

In the embodiments above and throughout, the spider may be made of rubber, as referenced, and the embodiments may use a traditional valve and seat. Of course, as indicated, the valve seat may be castellated with either channels (valleys) or ridges (high points) that keep the valve always open during a sudden flow change that causes the spider to push the multi-stage valve against the seat; and, as indicated, in such a case, the flow restrictor may be a ridged disk that maintains space between the valve seat and a flat surface of the spider. In the event of a surge flow, the spring in such embodiments may then be flexed "forward", such as responsive to pressure against the disk valve to which the spider is connected, toward the valve seat to reach the minimum flow until the pressure differential in the surge flow reduces to a "normal" flow condition. This flexure restriction prevents the blockage of the flow with debris in the aspirated fluid, as the ridges or channels maintain minimal flow and self-clearing as the flexure of the spider releases materials after the surge has passed.

FIG. 4 illustrates an exploded view of an additional embodiment of the multistage valve 400 described herein, and in accordance with the foregoing discussion. In the illustration, a valve seat 402 with castellation 404 (i.e., ribs) is shown at left. The bridged sealing surface 406 illustratively shown may set a minimum flow level, even in the event the valve "closes" due to a POS.

A spider membrane 410 is illustratively provided at center. The spider 410 shown may be a flexible membrane, such as a flexure-reed valve, which is "closed" against the sealing surface 406 in the event of high flow, i.e., in proportion to the flow. At normal flow conditions, the flow occurs around the spider 410. The filleted cross section sealing surface 406 determines the normal flow, and the spider 410 may experience a linear flexation such that it remains substantially neutral at normal flow. In a potential surge condition, the spider 410 flexes forward and presses against the castellated valve seat 402, thereby causing a substantially reduced flow. Thus, the embodiments may provide proportional fluidic resistance—that is, the greater the potential surge, the more the spider moves toward the castellated valve seat and "closes" the valve. The spider may be held in position by, and affixed to in order to provide a flexure base at multiple points along the outer periphery of the membrane, the aspiration flow inlet 420 shown at right.

In additional exemplary embodiments, the exemplary flow restrictor may be configured with or without a pressure transducer capability. By way of non-limiting example, a pressure sensor may be located "upstream" of the multistage valve in order to accurately measure and monitor intra ocular pressure (IOP).

Further, while the disclosed device may be located as close to the handpiece as possible, an exemplary flow restrictor may be located in a corresponded cassette, or within the tubing associated with the aspiration console, such as in order to reduce compliance fluid storage. Moreover, the embodiments may be provided along with smaller bore tubing, to thus correspondingly reduce the internal resistance of the tubing and thereby reduce the probability of a surge condition. Additionally, combining the disclosed flow restrictor with appropriately sized aspiration tubing and a corresponded surgical tip may allow the locating of the disclosed device farther from the handpiece and/or the patient's eye.

The skilled artisan will appreciate that aspirators may ultimately be built into the handpiece, and the disclosed flow restrictor may reduce or eliminate the need for vacuum adjustment, thus allowing for the smallest handpiece design. In the foregoing and other embodiments, irrigation may be supplied by gravity (such as from an elevated bottle), or pressurized infusion (such as by air pressure over a fluid), by way of non-limiting example.

The aspiration provided in the embodiments may be an all-electric solution, wherein a very small peristaltic or rotary vane pump is driven by a motor at the rear of the handpiece. A lighter-weight pump may be a venturi vacuum source driven through an air supply typical of vitrectomy probes. In any of the foregoing approaches, stability may be maintained by the disclosed variable flow restrictor.

Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure.

What is claimed is:
1. A flow restrictor suitable for inclusion in an aspiration flow of an ocular surgical device, comprising:
   a conical valve head suitable for insertion into a valve stage, wherein the conical valve head at least substan- tially impedes the aspiration flow when the conical valve head is at least partially inserted into the valve stage;

a flexible spider membrane having a plurality of valve passages that open and close with a flexation of the flexible spider membrane, wherein the flexible spider membrane is connective with the conical valve head and forces the insertion of the conical valve head into the valve stage proportionally to the aspiration flow;

a circular receiving plate for receiving the aspiration flow, wherein the circular receiving plate imparts the proportional insertion to the flexible spider membrane; and a plurality of ribs, integral to at least one of the conical valve head and the valve stage, that provides a minimum for the aspiration flow when the conical valve head is fully inserted into the valve stage.

2. The flow restrictor of claim 1, wherein the conical valve head remains uninserted upon aspiration reverse flow.

3. The flow restrictor of claim 1, wherein the circular plate comprises a base of the conical valve head.

4. The flow restrictor of claim 1, wherein the circular plate comprises a center passthrough of the spider membrane.

5. The flow restrictor of claim 4, wherein the passthrough is variably reactive to the aspiration flow.

6. The flow restrictor of claim 1, wherein a surface area of the circular plate is corresponded to a predetermined rate of the aspiration flow.

7. The flow restrictor of claim 1, wherein the conical valve head fully inserts into the valve stage upon a post-occlusion surge.

8. The flow restrictor of claim 1, wherein the conical valve head comprises the plurality of ribs on an outer surface thereof to maintain a minimal flow.

9. The flow restrictor of claim 1, further comprising at least one bumper situated to force the conical valve head out of the valve seat.

10. The flow restrictor of claim 1, wherein pressure fluctuations in an eye are minimized by the proportional insertion.

11. The flow restrictor of claim 1, wherein the plurality of valve passages are thinned.

12. The flow restrictor of claim 11, wherein the plurality of valve passages comprise a plurality of flow flaps.

13. The flow restrictor of claim 1, wherein each of the plurality of valve passages independently modifies a level of flow restriction.

14. The flow restrictor of claim 13, wherein the modifications are correspondent to the linear translation of each of the valve passages.

15. The flow restrictor of claim 1, wherein the spider membrane comprises rubber.

16. The flow restrictor of claim 15, wherein the valve passages change dimensionally as the rubber flexes.

17. The flow restrictor of claim 1, further comprising a luer fitting serially connected to the flexible spider membrane along the aspiration flow.

18. The flow restrictor of claim 1, wherein the plurality of ribs comprise waffle ribs.

19. The flow restrictor of claim 1, wherein the valve stage is rigid.

20. The flow restrictor of claim 1, wherein the spider membrane comprises a circumferential spring.

* * * * *